United States Patent [19]

Yamada et al.

[11] Patent Number: 4,944,427
[45] Date of Patent: Jul. 31, 1990

[54] DISPOSABLE TRAY FOR MEDICAL USE AND METHOD OF MAKING THE SAME

[75] Inventors: Hideaki Yamada, Kamakura; Masato Kimura; Masataka Oka, both of Fujisawa; Kohta Saito, Yokohama, all of Japan

[73] Assignee: Nippon Petrochemical Co., Ltd., Tokyo, Japan

[21] Appl. No.: 247,230

[22] Filed: Sep. 21, 1988

[30] Foreign Application Priority Data

Sep. 21, 1987 [JP] Japan .................. 62-143086
Dec. 4, 1987 [JP] Japan .................. 62-305761
Jul. 26, 1988 [JP] Japan .................. 63-184610

[51] Int. Cl.$^5$ .................. A61B 19/00
[52] U.S. Cl. .................. 220/406; 206/438
[58] Field of Search .............. 220/406, 405; 206/561, 206/438

[56] References Cited

U.S. PATENT DOCUMENTS

| | | | |
|---|---|---|---|
| 1,574,259 | 2/1926 | Sarff | 220/406 |
| 2,542,413 | 2/1951 | Ibsch, Jr. | 220/406 |
| 2,709,904 | 6/1955 | Boughton | 220/405 X |
| 3,305,124 | 2/1967 | Whiteford | 220/405 X |
| 3,362,604 | 1/1968 | Lagostina | 220/406 X |
| 4,523,679 | 6/1985 | Paikoff et al. | 206/438 X |

FOREIGN PATENT DOCUMENTS 48-30585 4/1973 Japan .
55-12062 1/1980 Japan .
62-502112 8/1987 Japan .

OTHER PUBLICATIONS

"Enue Verpackung", 8/79, pp. 896-899, Ein Neues System fur Sterile Warmgefomte Packungen.

Primary Examiner—Steven M. Pollard
Attorney, Agent, or Firm—Armstrong, Nikaido, Marmelstein, Kubovcik & Murray

[57] ABSTRACT

A disposable tray for medical use comprising at least two layers formed of thermoplastic resin. A first surface layer thereof is peeled to expose a sterile surface, and after use the tray can be disposed of by being folded into two. In use, liquid medicines are contained in recessed portions made in the tray, and medical instruments are placed to rest thereon. Filthy matters are placed in a large recessed portion of the tray.

16 Claims, 3 Drawing Sheets

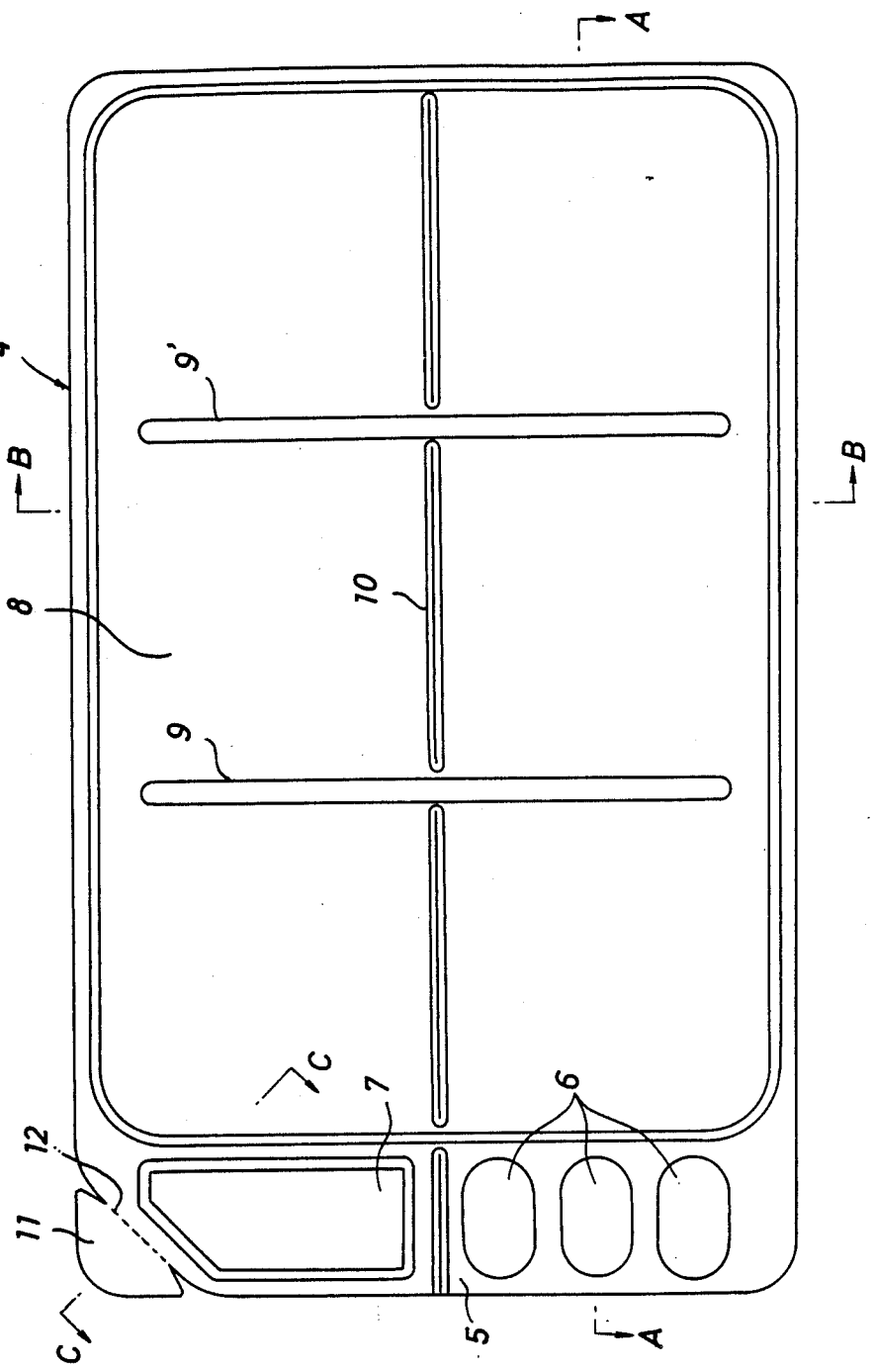

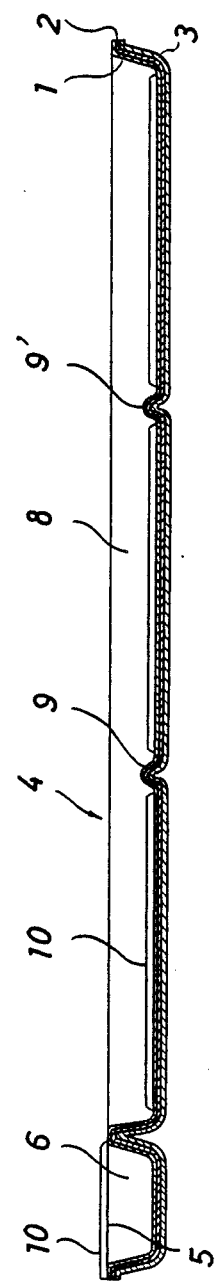
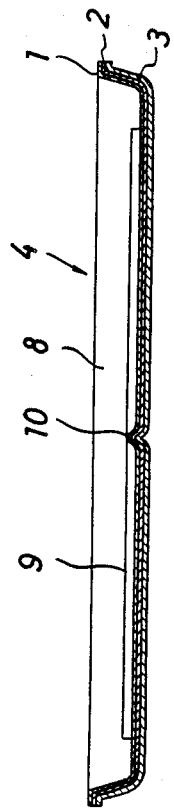

DISPOSABLE TRAY FOR MEDICAL USE AND METHOD OF MAKING THE SAME

BACKGROUND OF THE INVENTION

The present invention relates to a disposable thermoplastic tray for medical use which requires neither a cleaning operation nor sterilization treatment.

It has been typical hitherto that a tray used for keeping liquid medicines and medical instruments for a medical treatment therein is generally made of stainless steel or heat resisting synthetic resin. The conventional stainless steel tray is either sterilized by boiling immediately before its actual use or removed from a safe-keeping shelf in which it has been kept in a sterilized condition, and then put into medical use such as placing medicine bottles and sterilized medical instruments thereon.

However, the conventional tray described above is difficult to use since it must undergo sterilization by boiling, which is a troublesome and time-consuming process, each time it is used or a special facility has to be provided for keeping it sterile for later use. Also, there exists a sanitary problem in using the conventional tray in that it is possible for saliva or blood of other patients to get accidentally mixed up in the liquid medicines carried in the tray. Furthermore, in view of the more recent belief that one may be able to contract AIDS (Acquired Immunodeficient Syndrome) when receiving dental treatment or the like, it is very important to sanitize more thoroughly reusable articles or use disposable articles. Further, it is important to give a patient the impression that the medicine bottles and instruments used in medical treatment are all perfectly clean so that the patient is relieved of any possible psychological fear of getting infected with such a disease during the treatment.

OBJECT AND SUMMARY OF THE INVENTION

It is the object of the present invention to provide a disposable tray for medical use which is free from such disadvantages as an observed with the use of the conventional tray.

To achieve the above object, the present invention provides a disposable tray for medical use, which is characterized in that a tray body thereof comprises at least two layers formed of thermoplastic resin through a thermoforming process performed at a temperature of 150° C. or higher. A surface layer of the tray may be peeled from the next underlying layer, and includes recessed portions to contain liquid medicines therein and an instrument resting section for resting medical instruments thereon. The instrument resting section is provided with ridges to support the medical instruments. In the abovedescribed tray, there is also provided in the tray body another large recessed portion to keep filthy matters therein.

As a means to provide the tray with recessed portions, the tray body is formed so as to be rectangular in shape and includes a raised section formed at one end thereof in its longitudinal direction, in which section the recessed portions are provided. In order to make it convenient to carry the tray after use, the tray body is further provided with a folding groove so formed as to be perpendicular to said ridges and permit the tray to be folded into two while there is also provided at one end of the tray body a peel-off tab portion to facilitate peeling off the surface layer thereof. In addition, the tray is so formed that the bottom surfaces of the recessed portions and that of the instrument resting section are located on the same plane so as to make the tray rest stably on a treatment table or the like.

Preferably, the tray body is formed of three layers, of which the outermost layer is a layer compounded with at least one kind of additive or an organic filler, the intermediate layer is a layer compounded with neither an additive nor an organic filler, and the innermost or surface layer is a layer also not compounded with an additive nor an inorganic filler.

It is also preferable that the tray is characterized in that the peel-off strength of the upper surface layer from the next underlying layer is in the range of 30 to 200 g/20 mm W., and that the thickness of the upper surface layer is in the range of 0.01 to 0.5 mm. The thickness of the at least one underlying layer is in the range of approximately 0.2 to 5.0 mm.

The upper surface layer is different in color from the other layers so as to let one easily determine whether or not a particular tray has been used. To manufacture the tray, the tray body is made to consist of a multi-layer sheet formed through a co-extrusion molding process or of a multi-layer injection molded process with the upper surface layer thereof being made of lowdensity polyethylene and most of the underlying layers being made of polypropylene.

When the tray is to be used, the surface layer thereof is peeled off from the next underlying layer and the tray is then placed on a table or the like, and a necessary amount of each required liquid medicine is put into one of the recessed portions of the tray body. The newly exposed surface layer is now constituted by the former immediate underlying layer. Sterilized instruments can then be placed in the instrument resting section thereof. Filthy matters such as used gauze are kept in the large recessed portion provided for that purpose.

If the tray is provided with a folding groove to permit the folding of the tray body into two along the direction perpendicular to the ridges, the tray body is folded into two along said folding groove when the treatment is over, and then hand-carried to a disposal.

If the tray is provided with a peel-off tab portion at one end of the tray body, the surface layer is peeled off easily from the next underlying layer by holding the tab portion and pulling it.

When the surface layer of the tray body is colored differently from the other layers, the surface color is different between when the surface layer is peeled off and when it is yet to be peeled off, so that it can be easily distinguishable whether or not a particular tray has been already used.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1 is a general plan view of one embodiment of a tray for medical use according to the present invention;

FIG. 2 is a cross-sectional view of the embodiment shown in FIG. 1 taken along the line A—A;

FIG. 3 is a cross-sectional view of the embodiment shown in FIG. 1 taken along the line B—B;

DETAILED DESCRIPTION OF THE PREFERRED EMBODIMENT

Figure 4:
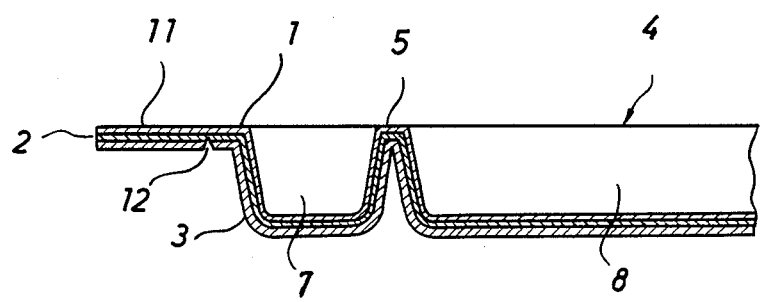
FIG. 4 is an enlarged cross-sectional view of the embodiment shown in FIG 1. taken along the line C—C thereof.

Now, embodying examples of the present invention will be explained in detail with reference to the accompanying drawings. In FIGS. 1–3, an embodiment of the present invention is shown in which the tray comprises three layers, each of which is made of thermoplastic resin. A first layer 1 constituting the upper surface layer ranges in thickness from 0.01 mm to 0.5 mm and is made of polyethylene, polypropylene, maleic anhydride modified polyethylene, maleic denatured polypropylene or the like while a second layer 2 and a third layer 3, which serve to hold the tray in its original shape, range in thickness from 0.2 mm to 5.0 mm, for instance, and are made of the same kind of resin such as polypropylene, polyethylene, polystyrene, polyvinyl chloride, polycarbonate, polyester, polyvinylidene chloride, polyvinyl alcohol, saponified ethylene vinylacetate copolymer product or polyamide.

All of these three layers 1, 2 and 3 are molded into a laminated structure by a co-extrusion process or the like which is carried out at a temperature of 150° C. or higher, which is required to get rid of bacteria and viruses, and is then formed into the shape of a tray by a thermoforming process in order to produce a tray body 4. Of these three layers, the first layer 1 constituting the upper surface layer and the second layer 2 constituting the next underlying layer are formed respectively of a suitable combination of thermoplastic resins selected from the above mentioned respective groups so that the peel-off strength may be in the range of 30–200 g/20 mm W., and so that the two layers can be peeled from each other when a peeling-off action is applied thereto, although they look integrally constructed in appearance.

Besides the second layer 2 and the third layer 3 serving to hold the tray in its original shape in the present embodiment example, the third layer 3 includes at least one kind of additive and compounding ingredient such as an antioxidant, an ultraviolet absorbent and/or the like for improving durability of the tray, an organic or inorganic pigment or dye for coloring the same, and calcium carbonate, talc or the like for increasing the rigidity thereof. The second layer 2 includes no such additives or compounding ingredients as included in the third layer, thereby minimizing the possible transfer of said additives or compounding ingredients therethrough. The first layer 1 constituting the original upper surface layer does not include such additives and compounding ingredients either so as to provide a perfectly clean surface of the tray body 4 after the first layer 1 is peeled off. If desired, the upper surface layer may be formed of a two-layer structure, the outer layer thereof including said additives or the like and the inner layer thereof including no additive, so that a new surface of the tray appearing after the original surface or the first layer 1 is peeled off may be kept substantially clean.

As described in the foregoing, the tray body 4 thermally formed in the shape of a tray is preferably rectangular shaped and includes a raised section 5 formed at one-end portion thereof in its longitudinal direction. The raised section 5 does not exceed in height the edge of the tray body, and in the raised section there are provided recessed portions 6 for keeping liquid medicines, and a comparatively large recessed portion 7 for containing filthy matter. Portions of the tray body other than said raised section 5 are used for resting instruments such as section 8. The upper surfaces of the instrument resting section and the recessed portion 7 are approximately in the same plane. The instrument resting section 8 has at two locations thereon instrument-supporting ridges 9, 9 so disposed in parallel to each other as to extend in the direction perpendicular to the longitudinal direction of the tray body. In addition, the tray body 4 has a folding groove 10 so provided as to extend along the longitudinal center line thereof so that the tray body can be folded laterally along said groove.

Figure 5:
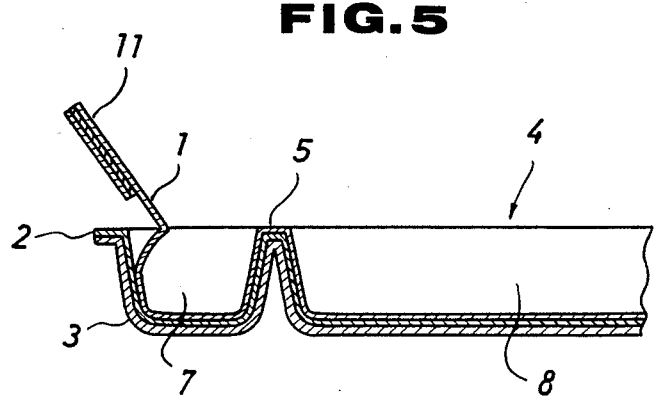
FIG. 5 is a cross-sectional view of the embodiment shown in FIG. 1 showing a condition in which the peel-off tab portion shown in FIG. 4 has been pulled upwards for peeling off the surface layer.

As shown in FIG. 4, a peel-off tab portion 11 is provided at one corner portion of the tray body 4 to facilitate peeling off the first layer constituting the surface layer. The tab portion 11 is formed so as to have a groove 12 extending through the third layer 3 and the second layer 2. The groove 12 does not extend through the first layer 1 so that the tab 11 is connected only to the first layer 1 so that the first layer 1 can be easily peeled off as indicated in FIG. 5.

In the foregoing example, the first layer 1 and the third layer 3 are colored differently from each other, for instance, the first layer in blue and the third in white, so as to allow one to easily determine whether or not the tray has already been used.

When the tray is going to be used, the tab portion 11 is pulled to peel off the first layer 1, which is the original surface layer. With the first layer 1 so removed, the second layer 2 is exposed with its surface in a sterile condition due to the molding process thereof. Thus, the newly exposed surface requires no sterilization treatment so that the tray can be immediately placed on a treatment table or the like ready for medical use such as holding required liquid medicines in its recessed portions 6 and to rest necessary medical instruments on the ridges 9, 9 in the instrument resting section 8 thereof. Used gauze or the like is placed and retained in the recessed portion 7.

Next, after the medical treatment is finished, the tray body 4 is folded into two so as to wrap up therein the used medical instruments. Afterwards, the tray with used medical instruments contained therein can be hand-carried to a place where used instruments are sterilized. After the instruments are removed from the tray body at that place, the tray now emptied of the medical instruments is then disposed.

In the foregoing embodiment example, the tray body is formed in the shape of a rectangle. However, the tray can be formed into any other suitable shape such as a circular or semicircular one.

More concrete examples of manufacturing a disposable tray for medical use according the present invention are described as follows:

EXAMPLE 1

Polypropylene having a melt flow rate (MFR) of 4.0 g/10 min. and a density, d of 0.91 g/cm$^3$ and known under the trade name of "NISSEKI POLYPROPYLENE J 130" (manufactured by Nippon Petrochemicals Co., Ltd.) was used as the thermoplastic resin for forming the second layer 2 and third layer 3. The resin for the third layer 3 was compounded with 0.3 Wt. % of an antistatic agent and 0.5 Wt. % of titanium white while the resin for the second layer 2 was compounded with neither of said additives. Low-density polyethylene having a MFR of 1.0 g/10 min. and a density of 0.92 g/cm$^3$ and known under the trade name of "NISSEKI REXLON F 22" (manufactured by Nippon Petrochemicals Co., Ltd.) was used as the thermoplastic resin for forming the first or upper surface layer 1, and was compounded with 0.2 Wt. % of a blue organic pigment. The laminar flows of the materials were joined together and melted in a die at a resin temperature of 240° C. and formed into a three-layer sheet by a co-extrusion process using a three-layer T-die, chill roll method.

As for the size of the sheet, the third layer 3 was 0.1 mm thick, the second layer 2 was 0.3 mm thick and the first or upper surface layer 1 was 0.1 mm thick.

Using a contact heating and vacuum forming process, the sheet obtained through the foregoing co-extrusion molding process was then formed under vacuum conditions at a preheating temperature of 160° C. into the shape of a tray measuring 250 mm in length, 140 mm in width and 11 mm in depth in such a way that the surface layer 1 constituted the inner wall of the tray. The tray was then cut along the outer periphery to form a cut-off edge, thereby obtaining the tray body 4 having the tab portion 11. Concurrently with the above edge cut-off operation, the third layer 3 and the second layer 2 were cut by a lower cutting edge to provide the tab portion 11 with the cut groove 12.

Using the above described tray body 4, a test specimen was prepared therefrom and tested for evaluating its peel-off strength and sterile condition. The peel-off strength was found to be 105 g/20 mm W., and when the tab portion 11 was bent backwards toward the inner side of the tray body 4, only the upper surface layer 1 covering the surface of the second layer of the tray body 4 was peeled off completely and easily from the surface of the second layer. Peeling was started from one end of the first layer and caused no deformation to the tray body 4. As for the sterile condition thereof, it was evaluated by using a thioglycollate culture medium for a sterile test prescribed under an antiseptic test method of the Japanese Pharmacopoeia in the following manner. After the surface layer 1 was peeled off, the thioglycollate culture medium was applied onto the tray body 4. The tray body was then left to remain for 7 days in an antiseptic box constantly maintained at 31° C. to observe visually whether or not bacteria would grow thereon. As a result of this observation, it was confirmed that the tray body 4 was kept clean by upper layer 1, because no growth of bacteria was observed.

EXAMPLE 2

For molding the second layer 2 and the third layer 3, polystyrene having a MFR of 2.7 g/10 min., and known under the trade name of "STYRON 475 D" (manufactured by Asahi Chemical Industry Co., Ltd.) was used as the thermoplastic resin to form the second layer 2 and the third layer 3. The third layer 3 was compounded with 0.3 Wt. % of an antistatic agent. For molding the upper surface layer 1, maleic anhydride modified polyethylene having a MFR of 0.8 g/10 min. and a density of 0.91 g/cm$^3$, and known under the trade name of "NISSEKI N POLYMER L 6033" (manufactured by Nippon Petrochemicals Co., Ltd.) was used as the thermoplastic resin to form the upper surface layer. The upper surface layer 1 was compounded with 0.2 Wt. % of a blue organic pigment. The laminar flows of these materials were joined together and melted in the die at the resin temperature of 200° C. and formed into a multi-layer sheet by a co-extrusion process using a two-layer T-die, chill roll method.

As for the size of the sheet, the second layer 2 and the third layer 3 were both 0.4 mm thick and the surface layer was 0.1 mm thick.

Using the foregoing described vacuum forming process, the sheet obtained through the foregoing described co-extrusion process was then thermally formed under vacuum conditions at the preheating temperature of 150° C. into the shape of a tray in such a way that the surface layer 1 of the sheet constituted the inner wall of the tray. The tray was then cut off along the outer periphery to form a cut-off edge, as in the Example 1, thereby obtaining the tray body 4 with the tab portion 11. Concurrently with the above cut-off operation, the third layer 3 and the second layer 2 were cut by a lower cutting edge to provide the tab portion 11 with the cut groove 12.

Using the above-described tray body 4, a test piece was prepared therefrom and tested to evaluate the peel-off strength and sterile condition thereof. The peel-off strength was found to be 160 g/20 mm W. and when the tab portion 11 was bent backwards toward the inner side of the tray body, only the surface layer 1 covering the surface of the second layer of the tray body 4 was easily peeled off. Peeling was started from one end of the layer and caused no deformation to the tray body 4. The sterile condition was checked in the same manner as in Example 1 with the results that the new surface of the tray body appearing after peel-off was maintained in a clean condition when covered by the peeled off layer.

EXAMPLE 3

For molding the second layer 2 and the third layer 3, polyvinyl chloride known under the trade name of "SHIN-ETSU PVC" (manufactured by Shin-Etsu Chemical Co., Ltd.) was used as the thermoplastic resin and was compounded with 0.3 Wt. % of an antistatic agent. For molding the upper surface layer 1, maleic denatured polyethylene having a MFR of 0.8 g/10 min. and a density of 0.91 g/cm$^3$, and known under the trade name of "NISSEKI N POLYMER L 6033" (manufactured by Nippon Petrochemicals Co., Ltd.) was used as the thermoplastic resin. The upper surface layer 1 was compounded with 0.2 Wt. % of a blue organic pigment. The laminar flows of these materials were joined together and melted in the die at the resin temperature of 190° C. and formed into a multi-layer sheet by a co-extrusion process using a two-layer T-die, chill roll method.

As to the size of the sheet, the second layer 2 and the third layer 3 were each 0.4 mm thick and the surface layer 1 was 0.1 mm thick.

Using the foregoing described vacuum forming process, the sheet obtained through the foregoing co-extrusion process was then thermally formed under vacuum conditions at the preheating temperature of 140° C. into the shape of a tray in such a way that the surface layer 1 of the sheet constituted the inner wall of the tray. The tray was then cut off along the outer periphery to form a cut-off edge, as in Example 1, thereby obtaining the tray body 4 with the tab portion 11.

Concurrently with the above described edge cut-off operation, the third layer 3 and second layer 2 were cut by a lower cutting edge to provide the tab portion 11 with the cut groove 12.

Using the above-described tray body 4, a test piece was prepared therefrom and tested to evaluate its peel-off strength and sterile condition. The peel-off strength was found to be 180 g/20 mm W., and when the tab portion 11 was bent backwards toward the inner side of the tray body, only the surface layer 1 covering the surface of the second layer of the tray body 4 was peeled off completely and easily. Peeling was started from one end of the layer and caused no deformation to the tray body 4. The sterile condition was checked in the same manner as in Example 1 with the results that the new surface of the tray body 4 appearing after peel-off was maintained in a clean condition by the peeled off layer.

As described in the foregoing, a disposable tray for medical use according to the present invention has such a construction that it can be readily put into medical use without undergoing any sterilization treatment. This eliminates a troublesome sterilization treatment applied to a conventional tray each time it is to be used, and eliminates the necessity of providing a special facility to keep the conventional tray in a sterilized condition. Thus, the use of the tray of the present invention has an economical advantage over the conventional tray.

Another advantage of the present invention is that a patient can see the thorough cleanliness of the tray for himself or herself, and will be completely relieved of the much talked-about fear of contracting AIDS while receiving a dental or surgical treatment, since the tray gets its surface layer peeled off under the eyes of the patient when it is to be used. Thus, the patient is given a strong impression of a high degree of cleanliness used in the dental or surgical treatment with the liquid medicines used for each patient being used strictly on an individual basis to ensure the best sanitation.

Additionally, according to the present invention, the tray has a groove provided to extend in the direction perpendicular to the ridges thereof so that the tray body can be folded into two after use to make it easy and convenient to hand-carry used instruments therein. A peel-off tab portion is also provided at one end of the tray body in order to facilitate peeling off the first layer which constitutes the original upper surface layer. The bottom surfaces of the recessed portions and that of the instrument resting section are so formed as to be on the same plane, thus enabling the tray to rest stably on a treatment table or the like. At the surface layer of the tray body and at least one other layer are colored differently from each other, it is easy to tell whether or not a particular tray has been used, so that there is no danger of erroneously using the same tray again, this being one advantage of the present invention.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:
1. A disposable tray for medical use, comprising:
a tray body formed of a coextrusion multi-layer sheet, said sheet comprising at least two layers formed of thermoplastic resin, said layers including an upper surface layer that can be peeled from the next underlying layer;
recessed portions provided in said tray body for containing liquid medicines therein; and
an instrument resting section provided on said tray for resting medical instruments thereon, said instrument resting section being provided with at least one ridge for supporting medical instruments.

2. A tray according to claim 1, wherein said tray body is substantially rectangularly shaped, and includes a raised section at one end portion thereof, in which said recessed portions are formed therein.

3. A disposable tray according to claim 2, wherein said tray body is provided with a groove along which said tray body can be folded into two, said groove extending in a direction substantially perpendicular to said at least one ridge.

4. A disposable tray according to claim 2, wherein a peel-off tab portion is provided at one end of said tray body so as to facilitate peeling off said upper surface layer.

5. A disposable tray according to claim 1, wherein said tray body is provided with a groove along which said tray body can be folded into two, said groove extending in a direction substantially perpendicular to said at least one ridge.

6. A disposable tray according to claim 5, wherein a peel-off tab portion is provided at one end of said tray body so as to facilitate peeling off said upper surface layer.

7. A disposable tray according to claim 1, wherein a peel-off tab portion is provided at one end of said tray body so as to facilitate peeling off said upper surface layer.

8. A disposable tray according to claim 1, wherein inner surfaces of said recessed portions and that of said instrument resting section are formed so as to be substantially in the same plane.

9. A disposable tray according to claim 1, wherein said tray body comprises three layers, the outermost one thereof being compounded with at least one kind of additive or inorganic filler, and the intermediate one thereof being compounded with neither an additive nor an inorganic filler.

10. A disposable tray according to claim 1, wherein the upper surface layer of said tray body is compounded with neither an additive nor an inorganic filler.

11. A disposable tray according to claim 1, wherein the thickness of said upper surface layer is in the range of approximately 0.01 to 0.5 mm, and that of said underlying layer portion is in the range of 0.2 to 5.0 mm.

12. A disposable tray according to claim wherein said upper surface layer is of a color different from that of said underlying layer.

13. A disposable tray according to claim 1, wherein the peel-off strength of said upper surface layer from said underlying layer is approximately 30 to 200 g/20 mm W.

14. A process for making a disposable tray for medical use, comprising the steps of:
combining by coextrusion at least two layers of thermoplastic resin to form a tray body in a manner that will allow one layer of said tray body to be peeled from another layer of said tray body; and forming recessed portions in the tray, wherein said at least two layers of thermoplastic resin are formed through a thermoforming process performed at a temperature of 150° C. or higher.

15. A process according to claim 14, wherein said layers are combined by a multi-layer injection molded process.

16. A disposal tray for medical use, comprising;

a tray body formed of a coextruded multi-layer sheet, said sheet comprising at least an upper surface layer and an underlying layer, said upper surface layer having a thickness in the range of approximately 0.1 to 0.5 mm and formed of a low density polyethylene that can be peeled from the next underlying layer, the peel-off strength associated with said upper and underlying layers is 30 to 200 g/20 mm W, said underlying layer having a thickness in the range of 0.2 to 5.0 mm and is formed of polypropylene;

recessed portions provided in said tray body adapted to contain liquid medicines; and an instrument resting section on said tray for resting medical instruments thereon, said instrument resting section being provided with at least one ridge for supporting medical instruments.

* * * * *

UNITED STATES PATENT AND TRADEMARK OFFICE
CERTIFICATE OF CORRECTION

PATENT NO. : 4,944,427

DATED : July 31, 1990

INVENTOR(S) : Hideaki YAMADA et al

It is certified that error appears in the above-identified patent and that said Letters Patent is hereby corrected as shown below:

Column 8, line 58, after "claim", insert -- 1 --.

Signed and Sealed this

Fifteenth Day of December, 1992

Attest:

DOUGLAS B. COMER

*Attesting Officer*      *Acting Commissioner of Patents and Trademarks*